United States Patent [19]

Nilubol

[11] Patent Number: 5,264,638
[45] Date of Patent: Nov. 23, 1993

[54] PROCESS FOR EXTRACTION AND PURIFICATION OF PLAUNOTOL

[75] Inventor: Naline Nilubol, Bangkok, Thailand

[73] Assignee: Chulalongkorn University, Bangkok, Taiwan

[21] Appl. No.: 826,702

[22] Filed: Jan. 28, 1992

[51] Int. Cl.$^5$ ...................... C07C 33/02; C07C 35/00
[52] U.S. Cl. .................................... 568/875; 568/816; 568/827; 568/822; 568/838; 568/840; 568/852; 568/857
[58] Field of Search ............... 568/875, 857, 816, 853, 568/852, 856, 822, 821, 840, 838, 868

[56] References Cited

U.S. PATENT DOCUMENTS 4,668,820  5/1987  Ibata et al. ..................... 568/875

FOREIGN PATENT DOCUMENTS 0139029  8/1982  Japan .................................. 568/857
0201736  11/1983  Japan .................................. 568/875
1149747  6/1989  Japan .................................. 568/875

Primary Examiner—Werren B. Lone
Attorney, Agent, or Firm—Townsend and Townsend Khourie and Crew

[57] ABSTRACT

A process for the extraction and purification of the diterpene alcohol Plaunotol from the leaves of the medicinal plant, *Croton sublyratus* Kurz. The process involves extracting firstly with a lower aliphatic alcohol followed by extracting from the alcohol solution with a chlorinated hydrocarbon. Then impurities are hydrolysed and the required Plaunotol separated by extraction with a hydrocarbon. This process is simple and gave much better yields than prior processes.

9 Claims, No Drawings

PROCESS FOR EXTRACTION AND PURIFICATION OF PLAUNOTOL

INTRODUCTION

Technical Field

This invention relates to a process for the extraction and purification of an acyclic diterpene alcohol called Plaunotol, of the following formula:

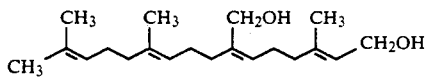

from the Thai medicinal plant "Plau-noi", identified as *Croton sublyratus* Kurz.

Background

Plaunotol has been isolated and its structure elucidated by spectral data and total synthesis together with several furanoditerpenes [(A. Agiso, et al., Chem. Pharm. Bull. 26,3117 (1978), and S. Roengsumran, J. of Nat. Prod., 45, No. 6 (1982), p772–773].

Plaunotol shows broad spectrum inhibition against acute gastric and duodonal ulcers and facilitates the healing of chronic gastric ulcer. The drug reduced the ulcer size and induced regeneration of mucosa, reduced the volume of gastric juice and also reduced acid and pepsin secretion. The compound facilitated biosynthesis of mucosal substances and prostaglandins in the mucosa and protected the break down of the mucous barrier and acted mainly on the mucosal site in the unchanged form [S. Kobayashi, et al., Pharmacometrics (Oyo Yakuri) 24,599 (1982) S. Okabe, et al., Pharmacometrics (Oyo Yakuri) 23,785 (1982); S. Kobayashi, et al., Prog. Med 5 (Supple. 1) 805 (1985)]. It showed no side effect or toxicity [H. Masuda, et al., Prog Med 5 (Supple. 1), 874 (1985); H. Masuda, et al., Prog. Med. 5 (Supple. 1), 881, (1985)].

Japanese Patent Specification Nos. 52-70010 and 57-139029 disclose extraction and purification processes for Plaunotol from *Croton sublyratus* Kurz, using solvents such as, for example, water, alcohols, ethers, esters, hydrocarbons, haloginated hydrocarbons and ketones, and purification by column chromatography on silica gel or alumina, with mixed organic solvents as the elutant. The process disclosed yielded from 0.50 to 0.73 g of Plaunotol per 1 Kg of dry leaves.

SUMMARY OF THE INVENTION

It is an object of the invention to provide an improved process for extracting Plaunotol.

This and other objects of the invention as will hereafter become more readily apparent have been achieved by providing a process for the extraction and purification of the diterpene alcohol known as Plaunotol of the formula:

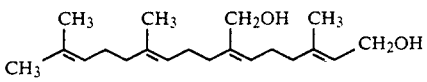

in which dried ground leaves of the Thai medicinal plant, "Plau-noi", *Croton sublyratus* Kurz are firstly extracted with a lower aliphatic alcohol, and then the extract is in turn extracted with a chlorinated hydrocarbon, the resultant extract is treated with a dilute alkali solution to hydrolyse unwanted compounds, and the desired Plaunotol is separated from the impurities by extraction with a hydrocarbon.

This process is simpler than that disclosed in the prior art and avoids the use of chromatography. Also the Plaunotol is produced in a good yield. Thus according to the invention yields of 1.5 to 2.0 g of Plaunotol per Kg of dry leaves is possible compared with 0.5 to 0.73 g per Kg by the prior process.

Solvents which can be used in the various steps of the process of the invention include $C_1$–$C_4$ monohydric aliphatic alcohols, such as methanol and ethanol, chlorinated hydrocarbons such as methylene chloride, chloroform and carbon tetrachloride, and hydrocarbons such as n-hexane, cyclohexane and heptane.

It is preferred to filter the hydrocarbon extract through an absorbent such as kieselguhr, diatomaceous earth, fullers earth or bentonite.

In one embodiment of the invention the chlorinated hydrobarbon extract is treated with activated carbon prior to hydrolysis.

The extraction of the leaves with the aliphatic alcohol can be carried out at a temperature from 60° to 80° C. for a period of 60 to 120 minutes in an agitated extracting vessel.

The following examples are offered by way of illustration and not by way of limitation.

EXAMPLE 1

6 Kg of dried leaves of Plau-noi, *Croton sublyratus* Kurz, were extracted with 60 l of methanol at 60° C. for 120 minutes in an agitated extracting vessel with a working volume of 60 l. The alcoholic extract was evaporated to almost dryness and the residue was extracted with 6 l of chloroform. About 400 g of activated carbon were added to the chloroform extract and the mixture stirred for 60 minutes. The carbon was removed by filtration and the filtrate was evaporated to dryness, yielding about 250 g of a semisolid residue.

The residue was dissolved in 3 l of an 80% ethanol/water (volume/volume) mixture and filtered. The filtrate was partitioned with 6 l of n-hexane and the ethanol layer was separated and evaporated to 1.5 l and 0.5 l of 10% aqueous sodium hydroxide solution was added. The mixture was heated at 110° C. for 15 minutes.

After the mixture had cooled to room temperature, 0.5 l of water was added and the mixture was extracted with 1.5 l of n-hexane. The organic phase was separated, dried over anhydrous sodium sulphate, filtered through a layer of 200 g of fullers earth and the solvent was distilled off giving 10.5 g of diterpene alcohol Plaunotol.

Infra red and proton nuclear magnetic absorption spectra of the product were identical with the spectra reported in the literature. $^{13}C$ NMR and mass spectrometer data also confirmed the structure of the compound as being Plaunotol.

EXAMPLE 2

The process of Example 1 was repeated, except that the decolourization step with activated carbon was omitted and the solution in 80% ethanol was centrifuged before filtration, giving the diterpene alcohol Plaunotol with similar yields.

EXAMPLE 3

The process disclosed in Example 1 of the Japanese Patent No. 52-70010 was repeated as follows.

6 Kg of dried ground leaves of Plau-noi, *Croton sublyratus* Kurz, were refluxed with 40 l of methanol. The methanol extract was evaporated leaving a crude extract which was dissolved in 1.0 l of 90% methanol and washed with n-hexane. The methanol layer was evaporated and the residue was suspended in 0.5 l of water and extracted with diethyl ether.

The ether layer was washed with a 5% solution of aqueous sodium carbonate and dried over anhydrous sodium sulphate. The solvent was evaporated leaving an oily residue which was purified by column chromatography over silica gel, eluting with ethyl acetate/benzene (10% by volume) and later with ethyl acetate/benzene (30% by volume). Fractions containing the active compound were combined and the solvent was distilled off leaving 3.4 g of the pure diterpene alcohol Plaunotol.

By comparing the yield of this Example which shows the prior art process with Examples 1 and 2 which are in accordance with the invention, it can be clearly seen that the processes of the present invention were simpler and gave a much better yield of the active compound.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for the extraction and purification of the diterpene alcohol known as Plaunotol of the formula:

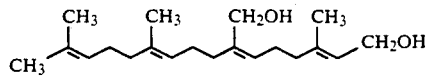

wherein dried ground leaves of the Thai medicinal plant, "Plau-noi" *Croton sublyratus* Kurz are first extracted with an unsubstituted lower aliphatic alcohol, and then the extract is turn extracted with a chlorinated hydrocarbon solvent, the resultant extract is partitioned between an unsubstituted lower aliphatic alcohol and a hydrocarbon solvent, the alcohol is treated with a dilute alkali solution to hydrolyze unwanted compounds, and the Plaunotol is separated from the impurities by extraction with a hydrocarbon solvent.

2. A process as claimed in claim 1 wherein the lower aliphatic alcohol is $C_1$ to $C_4$ monohydric aliphatic alcohol.

3. A process as claimed in claim 2 wherein the lower aliphatic alcohol is methanol or ethanol.

4. A process as claimed in claim 1 wherein the chlorinated hydrocarbon is methylene chloride, chloroform or carbon tetrachloride.

5. A process as claimed in claim 1 wherein the hydrocarbon is n-hexane, cyclohexane or heptane.

6. A process as claimed in claim 1 wherein the alcoholic extraction of the dried ground leaves is carried out at a temperature of from 60° to 80° C. for a period of 60 to 120 minutes in an agitated extracting vessel.

7. A process as claimed in claim 1 wherein the hydrocarbon extract of Plaunotol is filtered through an adsorbent.

8. A process as claimed in claim 7 wherein the adsorbent is kieselguhr, diatomaceous earth, fullers earth or bentonite.

9. A process as claimed in claim 1 wherein the chlorinated hydrocarbon extract is treated with activated carbon prior to hydrolysis.

* * * * *

UNITED STATES PATENT AND TRADEMARK OFFICE
CERTIFICATE OF CORRECTION

PATENT NO. : 5,264,638
DATED : November 23, 1993
INVENTOR(S) : Naline Nilubol

It is certified that error appears in the above-indentified patent and that said Letters Patent is hereby corrected as shown below:

On the title page, item [73], change "Taiwan" to --Thailand--.

Column 4, line 9, insert --in-- after "is".

Column 4, line 25, change "n-hexane" to --n-hexane--.

Signed and Sealed this

Twelfth Day of April, 1994

Attest:

BRUCE LEHMAN

*Attesting Officer*     *Commissioner of Patents and Trademarks*